United States

Häfeli 4,087,597

May 2, 1978

[54] ANTI-FOULING COMPOSITIONS

[75] Inventor: Robert Häfeli, Zurich, Switzerland

[73] Assignee: Biomarine Handelsgesellschaft AG., Vaduz, Liechtenstein

[21] Appl. No.: 730,719

[22] Filed: Oct. 8, 1976

[30] Foreign Application Priority Data

Oct. 17, 1976 Switzerland .................. 13530/76

[51] Int. Cl.² ............................................ C08K 5/18
[52] U.S. Cl. ................................. 526/5; 106/15 R; 526/6
[58] Field of Search ............... 424/257, 258, 329; 106/15 R; 260/279 R, 288 CF; 526/5, 6

[56] References Cited

PUBLICATIONS

Colour Index, 3rd edition, vol. 4, 1971, Society of Dyers & Colourists, pp. 4380 and 4382.

*Primary Examiner*—Paul R. Michl
*Attorney, Agent, or Firm*—Cushman, Darby & Cushman

[57] ABSTRACT

There is prepared an anti-foulant paint comprising a matrix of a synthetic resin containing (1) at least one metal toxicant, and (2) at least one of the following compounds:

(I) a salt of a mono- or diaminoacridine of the formula I

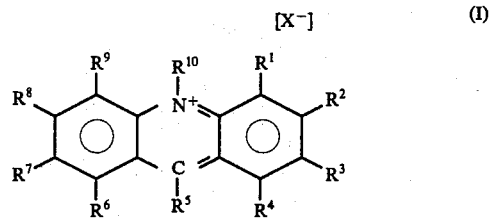

wherein $R^1$ is hydrogen, amino, methyl, ethyl, methoxy, chloro, nitro, or phenyl,
$R^2$ is hydrogen, amino, methyl, methoxy, chloro, nitro, or dimethylamino,
$R^3$ is hydrogen, amino, methyl, dimethylamino, methoxy, ethoxy, carbomethoxy, chloro, nitro, phenyl, cyano, or carbamyl,
$R^4$ is hydrogen, amino, methyl, methoxy, chloro, or nitro,
$R^5$ is hydrogen, amino, methylamino, β-hydroxyethylamino, or ω-aminoethyl,
$R^6$ is hydrogen, amino, or methyl,
$R^7$ is hydrogen, amino, methyl, methoxy, or chloro,
$R^8$ is hydrogen, amino, dimethylamino, nitro, or chloro,
$R^9$ is hydrogen, or methyl,
$R^{10}$ is hydrogen, or methyl, (II) salts of hexaalkyltriaminobenzenes of the formula II

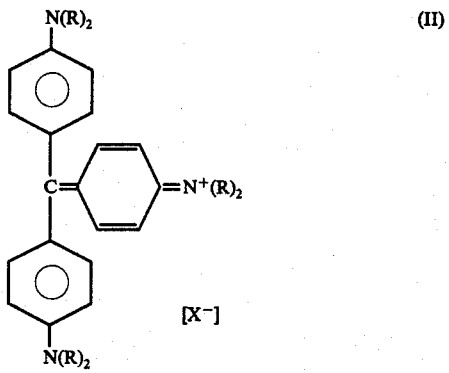

wherein R is hydrogen, methyl or ethyl, (III) salts of tetraalkyl-p-diaminotriphenyl carbinols of the formula III

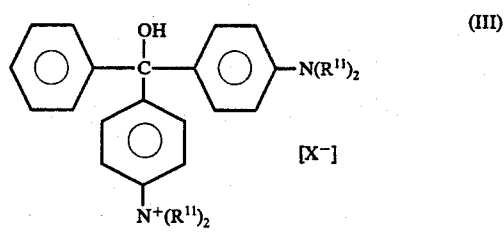

wherein $R^{11}$ is methyl or ethyl, (IV) copper complexes of β-alkylaminoalkylates of the formula IV, $R^{13}$-NH-$R^{12}$-CO-O-Cu-O-CO-$R^{12}$-NH-$R^{13}$, wherein $R^{13}$ is $C_nH_{2n+1}$ wherein n is an integer of from 12 to 22 and $R^{12}$ is -O- or -$C_mH_{2m}$- wherein m is an integer of from 2 to 4, (V) salts of 2,7-diamino-10-ethyl-9-phenyl phenanthridium,

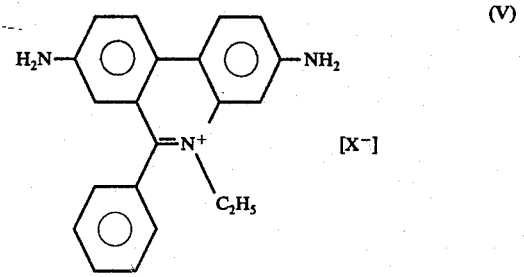

and X— is an anion in an amount effective to reduce the effect of sulphur producing bacteria on said metal toxicant.

9 Claims, No Drawings

ANTI-FOULING COMPOSITIONS

BACKGROUND OF THE INVENTION

The present invention relates to anti-fouling compositions, in particular for application to ships' bottoms and other surfaces to be immersed in water. The antifouling paints comprise a metal toxicant, e.g., cuprous or zinc oxide or an organotin compound, e.g, triphenyltin acetate or tributyltin oxide, dispersed in a matrix of synthetic resin, e.g., a vinyl chloride resin. Such compositions frequently include an activator for the toxicant, e.g., gum rosin.

The effectiveness of such compositions in inhibiting growth of slimes, algae, barnacles and other organisms depends upon progressive leaching from the composition of the toxic metal ion, leaving further metal available for continued toxic action, and in theory the composition sould continue to be effective until all the metal is exhausted.

It has been found, however, that the existing compositions cease to be effective before they should and we have discovered that this is due to the presence in the water of sulphur producing bacteria which convert copper or zinc oxide into the sulphide, a form in which it is no longer active against barnacles and the like. This is believed to be due to reduction by the bacteria to sulphide ions of sulphate ions present in sea water.

SUMMARY OF THE INVENTION

The invention is based on the discovery that this inhibiting effect on the bacteria can be obviated by inclusion in the composition of a small amount of a compound derived from one of the following classes:
(I) salts of mono- or diaminoacridines of the following formula I which is substituted or unsubstituted in the stated positions:

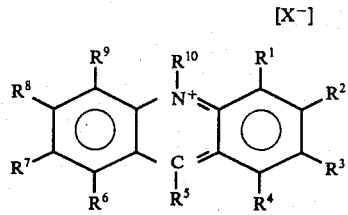

wherein $R^1$ is hydrogen, amino, methyl, ethyl, methoxy, chloro, nitro, or phenyl,
$R^2$ is hydrogen, amino, methyl, methoxy, chloro, nitro, or dimethylamino,
$R^3$ is hydrogen, amino, methyl, dimethylamino, methoxy, ethoxy, carbomethoxy, chloro, nitro, phenyl, cyano, or carbamyl,
$R^4$ is hydrogen, amino, methoxy, chloro, or nitro,
$R^5$ is hydrogen, amino, methylamino, $\beta$-hydroxyethylamino, or $\omega$-aminoethyl,
$R^6$ is hydrogen, amino, or methyl,
$R^7$ is hydrogen, amino, methyl, methoxy, or chloro,
$R^8$ is hydrogen, amino, dimethylamino, nitro, or chloro,
$R^9$ is hydrogen, or methyl,
$R^{10}$ is hydrogen, or methyl.

Preferred compounds of formula I are
(1) neutral chloride of 5-amino acridine
(2) acridine yellow (C.I. 46025)
(3) acridine orange (C.I. 46005)
(4) 2.8-diaminoacridine sulfate
(5) 2.7-diaminoacridine sulfate
(6) neutral chloride of 2.8-diamino-1.9-dimethyl acridine
(7) 2.8-diamino-1n-methacridinium hydroxide (as chloride).
(II) Salts of hexaalkyltriaminobenzenes of the formula II

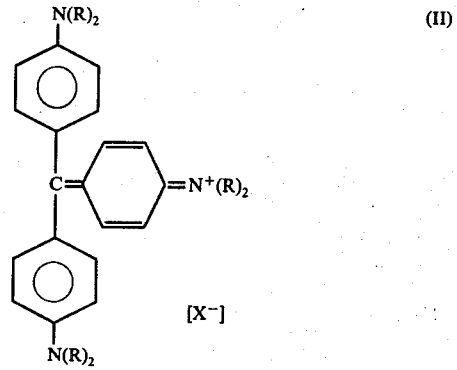

wherein R is hydrogen, methyl or ethyl. A preferred compound of the formula II is the color base of crystal violet (C.I. 42555) neutralised with distilled tall oil.
(III) Salts of tetraalkyl-p-diaminotriphenyl carbinols of the formula III

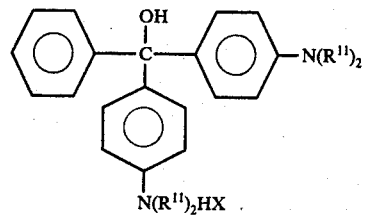

wherein $R^{11}$ is methyl or ethyl. Preferred compounds of the formula III are
(1) acetate salt of color base of malachite green (C.I. 42000)
(2) color base of brilliant green (C.I. 42040) neutralised with distilled tall oil. (IV) Copper complexes of $\beta$-alkylaminoalkylates of the formula IV, $R^{13}$—NH—$R^{12}$—CO—O—Cu—O—CO—$R^{12}$ —NH—$R^{13}$, wherein $R^{13}$ is $C_nH_{2n+1}$ wherein n is an integer of from 12 to 22 and $R^{12}$ is —O— or —$C_mH_{2m}$— wherein m is an integer of from 2 to 4.
Preferred compounds of the formula IV are:
(1) dodecyl-aminopropionate/copper complex
(2) hexadecyl-aminopropionate/copper complex
(3) dodecyl-amino-n-butyrate/copper complex.
(V) Salts of 2,7-diamino-10-ethyl-9-phenyl phenanthridium, such as chloride or bromide:

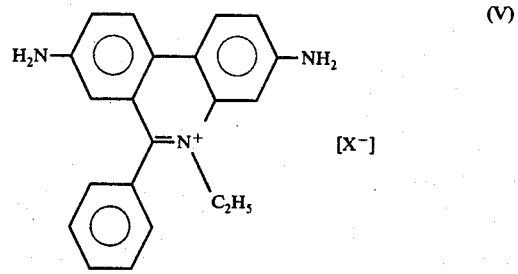

Preferred compounds of the formula V are:

(1) 2.7-diamino-10-ethyl-9-phenyl phenanthridium bromides
(2) 2.7-diamino-10-ethyl-9-phenyl phenanthridium chloride.

In the above formulae (I) to (III) and (V) $X^-$ is an anion, preferably chloride, sulphate/2, nitrate, formate, acetate, bromide, tallate or methyl sulphate ($H_3C-SO_3^-$).

Furthermore, it has been found that anti-fouling compositions of the invention comprising in addition an auxiliary controlling compound exhibit an improved activity. Preferred agents to be included into the anti-fouling compositions of the invention are, e.g.:

(A) Alkylol borate esters of the formula A, $B(OR_{13})_3$, wherein $R_{13}$ is $C_nH_{2n+1}$ wherein n is an integer of from 12 to 22, e.g., tris dodecyl borate or tris docosanyl borate;

(B) alkylammonium sulphamates of the formula B, $R_{14}(NH_3.SO_3.NH_2)$, wherein $R_{14}$ is $C_pH_{2p+1}$ wherein p is an integer of from 12 to 16, e.g., dodecylammonium sulphamate or hexadecylammonium sulphamate or (C) alkylamino alkylates of the formula C, $R_{15}NH—COOR_{16}$ wherein $R_{15}$ is $C_pH_{2p+1}$ (wherein p is an integer of from 12 to 16) and $R_{16}$ is $C_mH_{2m+1}$ wherein m is an integer of from 2 to 4, e.g., ethyl dodecylcarbamate or butyl hexadecylcarbamate.

In the anti-foulant paints of the invention, the novel compounds of the invention can be present, for example, in the following amounts, based on the metal toxicant:

Compounds of class I: 0.3 to 3% by weight
Compounds of class II: 1 to 5% by weight
Compounds of class III: 1 to 5% by weight
Compounds of class IV: 2 to 10% by weight
Compounds of class V: 0.3 to 5% by weight The auxiliary controlling compounds, when present, are normally used in the following amounts, based on the metal toxicant:
(A) 0.2 to 2% by weight
(B) 0.5 to 3% by weight
(C) 0.5 to 3% by weight Of course, less and higher amounts can be used. However, in general the above amounts are sufficient to obtain the desired effect.

The following examples illustrate the invention wherein the statements in "parts" are by weight, unless indicated.

DESCRIPTION OF THE PREFERRED EMBODIMENTS

EXAMPLE 1

An anti-fouling paint was prepared by dispersing in:

| | |
|---|---|
| 12 | parts vinyl chloride/vinyl acetate copolymer |
| 12 | parts xylene |
| 26 | parts 4-methylpentan-2-one |
| 2 | parts tri-butoxyethyl phosphate |
| 1.5 | parts acridine orange (C.I. 46005) |
| 0.5 | parts borate ester of mixed stearyl and cetyl alcohols |
| 0.7 | parts polymeric dispersing agent, e.g. linear condensation product of 2-naphthalene sulfonic acid and formaldehyde |
| 1.8 | parts gum rosin |
| both the following compounds: | |
| 42 | parts cuprous oxide |
| 1.5 | parts di-magnesium trisilicate |
| 100.0 | parts anti-fouling paint. |

This composition gives to surfaces coated with it a freedom from marine fouling for at least six months longer, under conditions of severe growth, than the period achieved by present state-of-the-art anti-fouling compositions.

EXAMPLE 2

An anti-fouling paint was prepared by dispersing in:

| | |
|---|---|
| 6.5 | parts vinyl chloride/vinyl acetate copolymer |
| 12.5 | parts xylene |
| 3 | parts gum rosin |
| 19 | parts 4-methylpentan-2-one |
| 1 | parts tri-tolyl phosphate |
| 3 | parts of the color base of brilliant green (C.I. 42046) |
| 4.5 | parts distilled tall oil, fraction 25–30* |
| 0.7 | parts polymeric dispersing agent, e.g. linear condensation product of 2-naphthalene sulfonic acid and formaldehyde |
| the following compound: | |
| 49.8 | parts cuprous oxide |
| 100.0 | parts anti-fouling paint. |

*trade description for a retired product, used in this case by Langley-Smith and Co. of London This composition gives to surfaces coated with it freedom from growth under severe conditions of marine fouling for at least six months.

EXAMPLE 3

An anti-fouling composition was prepared by dispersing in:

| | |
|---|---|
| 4.5 | parts gum rosin |
| 5.5 | parts vinyl chloride/vinyl acetate copolymer |
| 12.4 | parts xylene |
| 17.8 | parts 4-methylpentan-2-one |
| 2 | parts ethyl amyl ketone |
| 1 | parts acridine orange (C.I. 46005) |
| 1.5 | parts morpholine |
| 2 | parts tri-butoxyethyl phosphate |
| the following compound: | |
| 53.3 | parts cuprous oxide |
| 100.0 | parts anti-fouling paint. |

This composition gives to surfaces coated with it freedom from growth under severe conditions of marine fouling for at least eight months.

EXAMPLE 4

An anti-fouling paint was prepared by dispersing in:

| | |
|---|---|
| 5.5 | parts vinyl chloride/vinyl acetate copolymer |
| 4.5 | parts gum rosin |
| 1.8 | parts polybasic terpene acid polymer |
| 10.9 | parts xylene |
| 1.6 | parts tri-tolyl phosphate |
| 1.7 | parts of the color base of crystal violet (C.I. 42555) |
| 4.3 | parts distilled tall oil, fraction 25–30 |
| 1.5 | parts ethyl amyl ketone |
| 14.0 | parts 4-methylpentan-2-one |
| 1.2 | parts polymeric dispersing agent, e.g. linear condensation product of 2-naphthalene sulfonic acid and formaldehyde |
| the following compound: | |
| 53.0 | parts cuprous oxide |
| 100.0 | parts anti-fouling composition |

This composition gives to surfaces coated with it freedom from growth under severe conditions of marine fouling for at least seven months.

What is claimed is:

1. In an anti-fouling paint comprising in a matrix of synthetic resin (1) at least one metal toxicant, the improvement comprising including (2) at least one of the following compounds:
(I) a salt of a mono- or diaminoacridine of the formula I

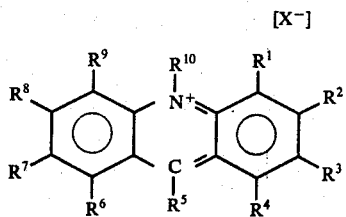     (I)

wherein $R^1$ is hydrogen, amino, methyl, ethyl, methoxy, chloro, nitro, or phenyl, $R^2$ is hydrogen, amino, methyl, methoxy, nitro, or dimethylamino, $R^3$ is hydrogen, amino, methyl, dimethylamino, methoxy, ethoxy, carbomethoxy, chloro, nitro, phenyl, cyano, or carbamyl, $R^4$ is hydrogen, amino, methyl, methoxy, chloro, or nitro, $R^5$ is hydrogen, amino, methylamino, $\beta$-hydroxyethylamino, or $\omega$-aminoethyl, $R^6$ is hydrogen, amino, or methyl, $R^7$ is hydrogen, amino, methyl, methoxy, or chloro, $R^8$ is hydrogen, amino, dimethylamino, nitro, or chloro, $R^9$ is hydrogen, or methyl, $R^{10}$ is hydrogen, or methyl, (II) salts of hexaalkyltriaminobenzenes of the formula II

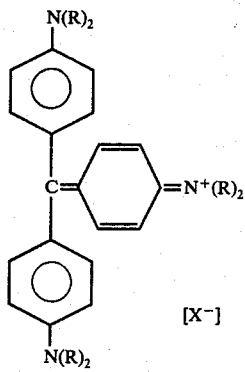  (II)

wherein R is hydrogen, methyl or ethyl, (III) salts of tetraalkyl-p-diaminotriphenyl carbinols of the formula III

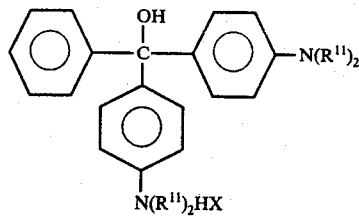

wherein $R^{11}$ is methyl or ethyl, (IV) copper complexes of $\beta$-alkylaminoalkylates of the formula IV, $R^{13}$—NH—$R^{12}$—CO—O—Cu—O—CO—$R^{12}$—NH—$R^{13}$, wherein $R^{13}$ is $C_nH_{2n+1}$ wherein $n$ is an integer of from 12 to 22 and $R^{12}$ is —O— or —$C_mH_{2m}$— wherein m is an integer of from 2 to 4, (V) salts of 2,7-diamino-10-ethyl-9-phenyl phenantridium,

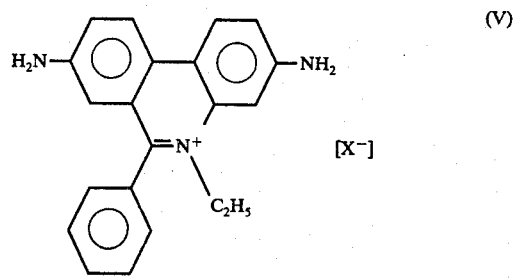  (V)

and X— is an anion in an amount effective to reduce the effect of sulphur producing bacteria on said metal toxicant.

2. An anti-fouling paint according to claim 1, wherein it comprises a compound of the formula I, II, III or V, wherein X— is a chloride, sulphate/2, nitrate, formate, acetate, tallate or methyl sulphate ($H_3C$—$SO_3^-$).

3. An anti-fouling paint according to claim 1 which also includes one of the following compounds:
(A) alkylol borate esters of the formula A, $B(OR_{13})_3$, wherein $R_{13}$ is $C_nH_{2n+1}$ wherein $n$ is an integer of from 12 to 22,
(B) alkylammonium sulphamates of the formula B, $R_{14}(NH_3.SO_3.NH_2)$ wherein $R_{14}$ is $C_pH_{2p+1}$ wherein $p$ is an integer of from 12 to 16 or
(C) alkylamino alkylates of the formula C, $R_{15}$—NH—$COOR_{16}$ wherein $R_{15}$ is $C_pH_{2p+1}$ wherein $p$ is an integer of from 12 to 16 and $R_{16}$ is $C_mH_{2m+1}$ wherein $m$ is an integer of from 2 to 4.

4. A ship bottom having its surface subject to immersion in water protected against the growth of slime, algae, and barnacles by having on its surface a coating of the anti-fouling composition of claim 1.

5. An anti-fouling paint according to claim 1 wherein (2) has formula (I).

6. An anti-fouling paint according to claim 1 wherein (2) has formula (II).

7. An anti-fouling paint according to claim 1 wherein (2) has formula (III).

8. An anti-fouling paint according to claim 1 wherein (2) has formula (IV).

9. An anti-fouling paint according to claim 1 wherein (2) has formula (V).